US00RE38386E

(19) United States
(12) Reissued Patent
Berman

(10) Patent Number: US RE38,386 E
(45) Date of Reissued Patent: Jan. 13, 2004

(54) RETARDATION OF METALLOPROTEINASE INCIDENTAL TO HIV AND/OR AIDS

(76) Inventor: Charles L. Berman, 211 Central Park West, New York, NY (US) 10024

(21) Appl. No.: 09/973,331

(22) Filed: Oct. 9, 2001

Related U.S. Patent Documents

Reissue of:
(64) Patent No.: 6,063,775
Issued: May 16, 2000
Appl. No.: 08/848,290
Filed: Apr. 29, 1997

(51) Int. Cl.[7] ..... A61K 31/65
(52) U.S. Cl. ..... 514/152
(58) Field of Search ..... 514/152

(56) References Cited

PUBLICATIONS

Lemaitre, et al., 112 CA 191459, 1990.
Wondrok, et al., 108 CA 179643, 1988.
Take, et al., 110 CA 147191, 1989.

*Primary Examiner*—Theodore J. Criares
(74) *Attorney, Agent, or Firm*—Stephen E. Feldman

(57) ABSTRACT

The instant invention provides a product of manufacture for retarding the biochemical formation of metalloproteinase, including gelatinase, elastase, collaginase, and the like, within the tissues of the body of a patient who has been inflicted with the HIV virus and/or the HIV virus which has advance to the AIDS virus, through the administration of an effective amount of a non-antimicrobial/non-antibiotic/non-antibacterial, chemically modified tetracycline (CMT) analog, its salts, cojugates and/or derivatives, and combinations thereof.

16 Claims, No Drawings

RETARDATION OF METALLOPROTEINASE INCIDENTAL TO HIV AND/OR AIDS

Matter enclosed in heavy brackets [ ] appears in the original patent but forms no part of this reissue specification; matter printed in italics indicates the additions made by reissue.

BACKGROUND OF THE INVENTION

*This is an application for the Reissue of U.S. Pat. No. 6,063,775, published May 16, 2000.*

The instant invention broadly relates to retardation of the biochemical formation of materials incidental to HIV and/or AIDS, which promotethe advancement of HIV to AIDS; which promote the advancement of AIDS and other opportunistic diseases to which a patient could inevitably succumb. Specifically, the invention retards the biochemical formation of species of metalloproteinase which are formed as a product of conditions such HIV and/or AIDS. Still more specifically, the invention provides for the administration of an effective amount of a drug which retards the biochemical formation of metalloproteinase species including coliagenase and gelatinase, incidental to the conditions of HIV and/or AIDS. Still even more specifically, the invention provides for the administration of an effective amount of a chemically modified tetracycline (CMT) analog which retards the biochemical formation of metalloproteinase species including gelatinase, collagenase and elastase, incidental to the conditions of HIV and/or AIDS.

Tetracyclines are useful as broad spectrum antibiotics because they have the ability to retard protein synthesis in a wide variety of bacteria. As disclosed in the above-identified pending patent applications, it has also been discovered that tetracyclines, antibiotic tetracyclines and non-antibiotic tetracyclines, have the ability to retard collagen-destructive enzymes, such as collagenase, responsible for the breakdown of connective tissue in a number of diseases, such as periodontal disease, corneal ulcers and rheumatoid arthritis.

The use of tetracycline antibiotics, while effective, may lead to undesirable side effects. For example, the long term administration of antibiotic tetracyclines may reduce or eliminate healthy flora, such as intestinal flora, and may lead to the production of antibiotic resistant organisms or the overgrowth of yeast and fungi.

Tetracycline may be a chemically modified tetracycline (CMT) or any tetracycline administered to a mammal in a dose that is effectively non-antimicrobial in the mammal. Preferably, the tetracycline is chemically modified so as to reduce its antimicrobial properties. Methods for reducing the antimicrobial properties of a tetracycline are disclosed in "The Chemistry of the Tetracyclines", Chapter 6, Mitscher, (1978), at page 211. As pointed out by Mitscher, modification a positions 1, 2, 3, 4, 10 and 12a lead to loss of bioactivity. The use of such modified tetracyclines is preferred in the present invention, since they can be used to higher levels than antimicrobial tetracyclines with fewer side effects.

The tetracycline molecule is amenable to substantial modification without losing its antibiotic properties. Examples of modifications that may and may not be made to the basic tetracycline structure have been reviewed by Mitscher in the Chemistry of Tetracyclines, Chapter 6. According to Mitscher, the substituents at positions 5–9 of the tetracycline ring, may be modified without complete loss of antibiotic properties. Changes to the basic ring system or replacement of the substituents at positions 1–4 and 10–12, however, generally lead to synthetic tetracyclines having substantially less or effectively no antibacterial activity. For example, 4-dedimethylaminotetracycline is commonly considered to be a non-antibacterial tetracycline.

U.S. Pat. No. 5,532,227 to Golub, et al teaches a method for treating mammals suffering from excessive extracellular protein glycosylation which is associated with diabetes, scleroderma and progeria by administering to the mammal a tetracycline which effectively inhibits excessive protein glycosylation.

Inhibition of metalloproteinase activity with various species of non-antimicrobial tetracycline, is well known in the prior art:

U.S. Pat. No. 5,321,017 to Golub, et al teaches a method for treating mammals suffering from rheumatoid arthritis and other tissue-destructive (chronic inflammatory or other) conditions associated with excess metalloproteinase activity which comprises: administering to the mammal an amount of a tetracycline that is effectively anti-metalloproteinase, but that is not effectively antimicrobial, and an amount of non-steroidal anti-inflammatory agent which, when combined with the effectively anti-metalloproteinase amount of tetracycline, results in a significant reduction of tissue destruction and/or bone loss.

U.S. Pat. No. 5,045,538 to Schneider, et al teaches a method for treating mammals suffering from skeletal muscle wasting and/or intracellular protein degradation of skeletal muscle systems by administering to the mammal an amount of tetracycline which results in a significant reduction of the muscle wasting and protein degradation. In addition, there is also disclosed a method of increasing the protein content of skeletal muscle systems of mammals by administration of tetracyclines. The tetracyclines useful in the above methods are both antimicrobial and non-antimicrobial. In a preferred embodiment, the method of treatment utilizes a non-antimicrobial tetracycline such as dedimethylaminotetracycline.

U.S. Pat. No. 5,324,634 to Zucker teaches diagnostic agents and methods for detecting the presence of metastatic activity in biological samples such as plasma. The agent and method preferably immunologically detect matrix metalloproteinases in complexed form with endogenous inhibitors of MMP's A kit for detecting the metalloproteinases is also disclosed.

U.S. Pat. No. 5,260,059 to Acott, et al relates to a method of treating ocular disease by modulating cellular secretion of a family of matrix metalloproteinases and their inhibitor. Specifically, differential stimulation of secretion of interstitial collagenase, gelatinase or type IV collaginase, stromelysin or proteoglycanase, and their tissue glycoprotein inhibitor is employed to treat open-angle glaucoma, retinal degeneration and detachment, ocular neovascularization and diabetic retinopathy.

U.S. Pat. No. 5,595,885 to Stetler-Stevenson, et al teaches an isolated protein of 21,600 Da which binds to both latent and activated type IV collagenase with high affinity at 1:1 molar stoichiometry, thereby abolishing enzyme activity. The protein is purified by affinity chromatography on solid phase metalloproteinase, or solid phase metalloproteinase substrates which bind the enzyme-inhibitor complex. The complete primary structure of this protein (initially called CSC-21K), as determined by sequencing overlapping peptides spanning the entire protein, reveals homology with a protein called TIMP, Tissue Inhibitor of Metalloproteinases. In addition, a cDNA for this novel inhibitor, now designated TIMP-2, was cloned from a melanoma cell and its sequence was compared with that of human TIMP-1. Northern blots of melanoma cell mRNA showed two distinct transcripts of 0.9 kb and 3.5 kb which are down-regulated by transforming growth factor-beta, and are unchanged by phorbol ester treatment. The inhibitor of the present invention may be used for treatment of pathologic conditions resulting from inappropriate degradation of extracellular matrix molecules by matrix metalloproteinases, such as metastatic neoplasia, myocardial infarction, and arthritis. Therapeutic treatments using this inhibitor may include formulations for inhalation and inclusion complexes adapted for buccal or sublingual administration, or administration of a recombinant DNA molecule which expresses a DNA segment that encodes the matrix metalloproteinase inhibitor of this invention.

U.S. Pat. No. 5,308,839 to Golub, et al teaches a method for treating mammals suffering from rheumatoid arthritis, other tissue-destructive conditions, and chronic inflammatory or other conditions associated with excess metalloproteinase activity which comprises: administering to the mammal an amount of a tetracycline that is effectively anti-metalloproteinase, but that is not effectively antimicrobial, and an amount of a non-steroidal anti-inflammatory agent which, when combined with the effectively anti-metalloproteinase amount of tetracycline, results in a significant reduction of tissue destruction and/or bone loss.

U.S. Pat. No. 5,532,227 to Golub, et al teaches a method for treating mammals suffering from excessive extracellular protein glycosylation which is associated with diabetes, scleroderma and progeria by administering to the mammal a tetracycline which effectively inhibits excessive protein clycosylation.

U.S. Pat. No. 5,308,839 to Golub, et al teaches a method for treating mammals suffering from rheumatoid arthritis, other tissue-destructive conditions, and chronic inflammatory or other conditions associated with excess metalloproteinase activity comprising administering to the mammal an amount of a tetracycline that is effectively anti-metalloproteinase, but that is not effectively antimicrobial, and an amount of a non-steroidal anti-inflammatory agent which, when combined with the effectively anti-metalloproteinase amount of tetracycline, results in a significant reduction of tissue destruction and/or bone loss.

U.S. Pat. No. 5,223,248 to McNamara et al teaches a method of inhibiting plaque formation on mammalian tooth surfaces. The method includes contacting the tooth surfaces with an effective amount of a non-antibacterial tetracycline. In a preferred embodiment, such tetracyclines are included in various oral hygiene products such as dentifrices, lozenges, chewing gums and the like to contact the tooth surfaces and prevent plaque accumulation thereon.

U.S. Pat. No. 5,045,538 in Schneider, et al teaches a method for treating mammals suffering from skeletal muscle wasting and/or intercellular protein degradation of skeletal muscle systems by administering to the mammal an amount of tetracycline which results in a significant reduction of the muscle wasting and protein degradation. In addition, there is also disclosed a method of increasing the protein content of skeletal muscle systems of mammals by administration of tetracyclines. The tetracyclines useful in the above methods are both antimicrobial and non-antimicrobial. In a preferred embodiment, the method of treatment utilizes a non-antimicrobial tetracycline such as dedimethylaminotetracycline (CMT).

Generally, tetracyclines, as has now been discovered, whether possessing antimicrobial or antibiotic activity or not, all possess anti-collagen-destructive enzyme activity or anti-collagenase activity. They are known to inhibit the activity of collagen destructive enzymes such as mammalian collagenase, macrophage elastase and bacterial collagenase; Golub et al., J. Periodont. Res. 20, 12–23 (1985), Golub et al., Crit. Revs. Oral Biol. Med. 2, 297–332 (1991). Collagen is a major component of connective tissue matrices such as those in bone, synovium, eye, skin, tendons and gingiva. Collagenase, which is naturally produced by only a few types of bacteria and in a number of tissues and cells in mammals, degrades collagen.

This anti-collagenase activity appears to be attributable to the unique structure of tetracyclines, i.e. the special four carbocyclic ring structure which is characteristic of and possessed by the tetracyclines.

As an observation, it is believed that the carbonyl moieties in the carbocyclic ring nucleus of the tetracycline are important to the anti-collagenolytic activity of these compounds because they chelate the metal ions calcium and zinc. This is an important property since the collagenolytic enzymes mentioned are metal dependent.

It is known that antimicrobial and non-antimicrobial tetracyclines can bind to metal ions such as calcium.

Tetracyclines are also known retarders of collagen destructive enzymes such as mammalian collagenase, a calcium dependent zinc-metalloproteinase. Collagen is a major component of connective tissue matrices such as those in the bone, synovium, eye, skin, tendons and gingiva but not tooth surface enamel.

In the case of mammalian collagenase, degradation of collagen is a natural part of the normal growth-degradation-regeneration process that occurs in connective tissue. The production of collagenase, however, may become excessive. Such excessive collagenase production often results in the pathologic and debilitating destruction of connective tissue.

It is well known that metalloproteinases which include collogenases are produced as byproducts of HIV and AIDS.

It is known that HIV-infected monocytes form highly invasive network on basement membrane matrix and secrete high levels of 92-kd metalloproteinase (MMP-9), an enzyme that degrades basement membrane proteins. In a study, using matrigel as a model basement membrane system, it was demonstrated that treatment of human immunodeficiency virus HIV-infected monocytes with interferon-gamma at 50 U/ml inhibited the ability of infected monocytes to form an invasive network on matrigel and their invasion through the matrigel matrix. These effects were associated with a significant reduction in the levels of MMP-9 produced by HIV-infected monocytes treated with interferon-gamma 1 day prior to infection with HIV as compared with that of untreated HIV-infected monocytes. Monocytes treated with interferon-gamma 1 day after HIV infection showed the presence of integrated HIV sequences; however, the levels of MMP-9 were substantially lower than those produced by monocytes inoculated with live HIV, heat-inactivated HIV, or even the control uninfected monocytes. Exposure of monocytes to heat-inactivated HIV did not result in increased invasiveness or high MMP-9 production, suggesting that regulation of metalloproteinase by monocytes was independent of CD4-gp 120 interactions and required active virus infection. Furthermore, addition of interferon-gamma to monocytes on day 10 after infection inhibited MMP-9 production by more than threefold with no significant reduction of virus replication. It was concluded that these results indicate that the mechanism of interferon-gamma-induced down-regulation of MMP-9 levels and reduced monocyte invasiveness may be mediated by a mechanism independent of antiviral activity of IFN-gamma in monocytes. Down-regulation of MMP-9 in HIV-infected monocytes by interferon-gamma may play an important role in the control of HIV pathogenesis.

It has further been reported that monocytes are susceptible to HIV infection and to activation by a regulatory gene product of the HIV genome, HIV-Tat. Recently, it was demonstrated that treatment with HIV-Tat up-regulates monocyte adhesion to the endothelium and increases metalloproteinase production in the present study, the ability of the HIV-Tat protein to alter the migratory and invasive behavior of monocytes were examined. Monocytes pretreated for 24 hours with 10 ng/ml HIV-Tat exhibited enhanced migratory behavior compared with untreated monocytes in chemotaxis assays, both in the absence of a chemoattractant as well as in response to FMLP in addition, HIV-Tat itself induced the migration of both untreated and HIV-Tat pretreated monocytes. Checkerboard analysis showed that monocytes migrated in response to an HIV-Tat concentration gradient, thus confirming the chemotactic characteristics of the HIV-Tat protein. Pretreatment of monocytes with 10 ng/ml HIV-Tat for 24 h also increased their ability to invade reconstituted extracellular membrane (Matrigel)-coated filters by 5-fold in the absence of chemoattractant. The presence of FMLP or HIV-Tat further enhanced invasion by both untreated and HIV-Tat-pretreated monocytes by more than 10-fold. Monocyte invasion was partially inhibited by the inclusion of anti-beta integrin Ab or tissue inhibitor of metalloproteinase (TIMP). Thus, for the first time, evidence was provided that HIV-Tat can enhance the chemotactic and invasive behaviors of monocytes and propose an active role for HIV-Tat in the recruitment of monocytes into extravascular tissues, a process which may contribute to the destruction of tissues and cellular architecture often seen in patients with acquired immunodeficiency syndrome.

It was further demonstrated HIV infection of monocytes resulted in twofold elevation of adhesion molecule LFA-1 (both alpha L/CD11a and beta 2/CD18 subunits) and LFA-3 (CD58), with no apparent increase in LFA-2 (CD2) or various beta 1-integrins. Homotypic aggregation of monocytes was evident 2 hours after exposure to virus and was inhibited by mAbs to both the alpha L- and beta 2-subunits of LFA-1. HIV-infected monocytes also showed a marked increase in adherence to brain capillary endothelial cell monolayers derived from brain, lung, and skin. This adherence was inhibited by mAb to either LFA-1 subunit and by mAb to the counter-receptor intercellular adhesion molecule-1. Cocultivation of HIV-infected monocytes with endothelial cells increased permeability of endothelial cell monolayers to 125I albumin in transwell assay systems. The increased endothelial permeability induced by HIV-infected monocytes was associated with a substantial disruption of the endothelial cell monolayer. Morphologic disruption was not a direct toxic effect on endothelial cells, but appeared to be secondary to changes in endothelial cell-cell to cell-matrix interactions. Northern blot analysis showed increased expression of gelatinase B (92-kDa gelatinase), tissue inhibitor of metalloproteinase TIMP-1, and TIMP-2 in the-infected monocytes. Consistent with these Northern analyses, secretion of gelatinase activity in culture fluids of HIV-infected monocytes was also increased and was dependent on the staage of virus replication. Incubation of HIV-infected monocytes with the proteinase inhibitors TIMP-1 and TIMP-2 inhibited the increased permeability of endothelial cell monolayers to 125I albumin. These results suggest possible mechanisms for extravasation of HIV-infected monocytes through vascular endothelium into tissue in early stages of HIV disease.

SUMMARY OF THE INVENTION

The instant invention in large part solves the problems of the prior and fulfills a long felt need by providing a drug in a dosage sufficient for effectively retarding the biochemical formation of metalloproteinase within the bodies of patients inflicted with HIV and/or AIDS viruses.

Here are the more important features of the invention as broadly outlined, in order that the detailed description that follows may be better understood; and in order for the present contribution to the art may be better appreciated. There are additional features of the invention that will be described hereinafter and which form the subject matter of the appended claims. Those of ordinary skill in the art will appreciate that the conception upon which this disclosure is based may readily be utilized as a basis for the designing of other structures, methods and systems for carrying out the several purposes of the instant invention. It is important, therefore, that the claims be regarded as including such equivalent constructions insofar as they do not depart from the spirit and scope of the instant invention.

Further, the purpose of the instant abstract is to enable the U.S. Patent and Trademark office and the public generally, and especially the scientists, engineers and practitioners in the art who are not familiar with parent or legal terms or phraseology, to determine quickly from a cursory inspection of it, the technical disclosure of the patent application. The abstract is neither intended to define the invention of the instant patent application, which is measured by the claims, nor is it intended in any manner to be limiting as to the scope of the instant invention.

The instant invention in large part solves the problems of the prior and fulfills a long felt need by providing a treatment for a patient with HIV and/or AIDS.

The instant invention provides a drug in a dosage sufficient for treating a patient who has been inflicted with the HIV and/or AIDS viruses, with an effective dosage of a non-antimicrobial/non-antibiotic/non-antibacterial, drug in the body of the patient.

The instant invention provides a drug to a dosage sufficient for treating a patient who has been inflicted with the HIV and/or AIDS viruses, with an effective dosage of a non-antimicrobial/non-antibiotic/non-antibacterial, chemically modified tetracycline (CMT) analog in the body of the patient.

The instant invention provides a drug in a dosage sufficient for treating a patient who has been inflicted with the HIV and/or AIDS viruses, with an effective dosage of a non-antimicrobial/non-antibiotic/non-antibacterial, chemically modified tetracycline (CMT) sufficient to retard the biochemical formation of metalloproteinase within the body of the patient.

The instant invention provides a drug in a dosage sufficient for treating a patient who is inflicted with the HIV and/or AIDS viruses, with an effective dosage of a non-antimicrobial/non-antibiotic/non-antibacterial, chemically modified tetracycline (CMT) analog effective to retard the biochemical formation of metalloproteinase within the body of the patient.

The instant invention provides a drug in a dosage sufficient for treating a patient who is inflicted with the HIV and/or AIDS viruses, with an effective dosage of a chemically modified tetracycline (CMT) analog sufficient to retard the biochemical formation of gelatinase, elastase, collaginase, and the like, within the tissues of the body of the patient.

The instant invention provides a drug to a dosage sufficient for treating a patient who is inflicted with the HIV and/or AIDS viruses, with an effective dosage of a non-antimicrobial/non-antibiotic/non-antibacterial, chemically modified tetracycline (CMT) analog sufficient to retard the biochemical formation of gelatinase, elastase, collaginase, and the like, within the tissues of the body of the patient.

The instant invention provides a drug in a dosage sufficient for treating a patient who is inflicted with the HIV and/or AIDS viruses, with an effective dosage of a non-antimicrobial/non-antibiotic/non-antibacterial, chemically modified tetracycline (CMT) analog sufficient to retard the biochemical formation of gelatinase, elastase, collaginase, and the like, within the tissues of the body of the patient.

Other objects, features, and advantages of the instant invention, in its details of construction and arrangement of parts, will be seen from the above, from the following description of the preferred embodiment when considered in light of the appended claims.

DETAILED DESCRIPTION OF THE INVENTION

The instant invention provides a drug in a dosage sufficient for retarding endrogenous metalloproteinase and at least its species of elastase, collagenase and gelatinase, characterized by that occurring in the body of a patient who has become inflicted with the HIV virus and/or treating a patient who has become infected with the HIV virus which has progressed to AIDS. The instant invention contemplates administering to the patient an effective dosage of an analog of chemically modified tetracycline (CMT) selected from the group consisting of: 4-dedimethylaminotetracycline, 4-dedimethylamino-5-oxytetracycline, 4-dedimethylamino-7-chlortetracycline, 4-hydroxy-4-dedimethylaminotetracycline, 5a, 6-anhydro-4hydroxy-4-dedimethylaminotetracycline, 6alpha-deoxy-5-hydroxy-4-dedimethylaminotetracycline, 6-demethyl-6-deoxy-4-dedimethylaminotetracycline, 4-dedimethyaminno-11-hydroxy-12a-deoxytetracycine, 12a-deoxy-4-deoxy-4-dedimethylaminotetracycline, 6alpha-deoxy-5-hydroxy-4-dedimethylaminotetracycline, 12a,4a-anhydro-4-dedimethylaminotetracycline, minocycline-CMT, 7-dimethylamino-6-demethyl-6-deoxy-4-dedimethylaminotetracycline, 6a-benzylthiomethylenetetracycline, the 2-nitrilo analogs of tetracycline (tetracyclinonitrile), the mono-N-alkylated amide of tetracycline; 6fluoro-6-demethyltetracycline, 11a-chloroletracycline, tetracycline pyrazole, 12a-deoxytetracycline and its derivatives, 4-dedimethylamino-5oxytetracycline, 5a, 6-anhydro-4-hydroxy-4-dedimethylaminotetracycline, 12a,4a-anhydro-4-dedimethylaminotetracycline, tetracyclinonitrile, 7-chloro-4-dedimethylaminotetracycline, 12a-deoxy-4-deoxy-4-dedimethylaminotetracycline, 4-dedimethylamino-7chlorotetracycline, 4-dedimethylamino-7-dimethylamninoletracycline, the 2-nitrilo analogs of tetracycline, 4-dedimethylamino-12a-deoxytetracycline and its derivatives, tetracyclines altered at the 2 carbon position to produce a nitrile, 4-de-dimethylamino-7-chlorotetracycline, 6-alpha-deoxy-5-hydroxy-4-dedimethylaminotetracycline, tetracyclinotrile, 6-alpha-benzylthiomethylenetetracycline, the 2-nitrilo analog of tetracycline, 11 alpha-chlorotetracycline, 7-chlorotetracycline, 5-hydroxytetracycline, 6-demethyl-7-chlorotetracycline, 6-demethyl,-6-deoxy-5-hydroxy-6-methylenetetracycline, 6-alpha-benzylthiomethylenetetracycline, a nitrite analog of tetracycline, a mono-N-alkylated amide of tetracycline, 11-alpha-chlorotetracycline, 2-acetyl-8-hydroxy-1-tetracycline, 6-demethyl-6-deoxytetracycline, 6-demethyl-6-deoxy-5-hydroxy-6-methylenetetracycline, 2-acetyl-8-hydroxyl-1-tetracycline, 4-hydroxy-4dedimethylaminotetracycline, 5a,6-anhydro-4-hydroxy-4dedimethylaminotetracycline, 6-demethyl-6-deoxy-4-dedimethylaminotetracycline, 6-deoxy-6-demethyl-4-dedimethylaminotetracycline, 6a-deoxy-5-hydroxy-4-dedimethylaminotetracycline, Tetracyclines altered at the 2-carbon position to produce a nitrile, pyrazole derivative of tetracycline, 7-chloro-6-demethyl-4-dedimethylaminotetracycline, 11 alpha-chlortetracycline, 4-dedimethylamino-7-chlortetracycline, 4-de(dimethylamino)-tetracycline, 4-de(dimethylamino)-5-oxytetracycline, 4-de(dimethylamino)-7-chlortetracycline, 11 alpha a-chlortetracycline, 7-chloro-6-demethyl-4-dedimethylaminotetracycline, 6-o-deoxy-5-hydroxy-4-dedimethylaminotetracycline, 6-alpha-obenzylthiomethylenetetracycline, 4-de(dimethylamino-5-oxytetracycline, 4-de(dimethylamino)-7-chlorotetracycline, 4-hydroxy-4-dedimethylaminotetracycline, 6-alpha-deoxy-5-hydroxy-4-dedimethylamino-tetracycline, 4-de(dimethylamino) tetracycline, 4-de(dimethylamino)-7 chlorotetracycline, 7-chloro-6-demethyl-4-dedimethylamino-tetracycline, dedimethylaminotetracycline, a 6-alpha-benzylthiomethylene tetracycline, 6-alpha benzylthiomethylene tetracycline, an 11-alpha-chlortetracycline, 6-demethyl-6-deoxy-5-hydroxy-6-methylenetetracycline, a 6 alpha-benzylthiomethylene tetracycline, and a 6 Fluoro demethyltetracycline, their salts, cojugates and/or derivatives, and combinations thereof.

The analog of the instant invention may be administered orally, or systemically, or by way of an injection or intravenously. It may also be administered topically in the form of an ointment, or other storable topical delivery system, i.e., applying it with a highly adsorptive material such as DMSO.

Dosages of the analog can range in amounts of from about 0.1 mg/kg/day to about 50 mg/kg/day, more preferably in amounts of from about 10.0 mg/kg/day to about 30 mg/kg/day; and most preferably amounts of about 20.0 mg/kg/day to about 25.0 mg/kg/day.

The preferred pharmaceutical composition for use in the present invention comprises a combination of the chemically modified tetracycline (CMT) and the anti-inflammatory agent in a suitable pharmaceutical carrier. The means of delivery of the pharmaceutical carrier with active may be in the form of a capsule, compressed tablet, pill, solution or suspension suitable for oral administration to a mammal. Other means of delivery include a gel for topical application for corneal ulcers, periodontal disease, etc. It is contemplated that carriers be included which are suitable for administration orally, topically, by injection into a joint, and by other selected means.

The non-steroidal anti-inflammatory agent may be selected from the various classes of such compounds. Such classes include, for example, salicylates such as acetylsalicyclic acid and diflunisal, acetic acids such as indomethacin, sulindac, tolmetin, diclofenac, and etodolac; propionic acids such as flurbiprofen, naproxen, and ketoprofen; fenamates such as meclofenamate; and oxicams such as piroxicam.

The preferred non-steroidal anti-inflammatory agents include flurbiprofen, piroxicam, tolmetin sodium, ibuprofen, naproxen and indomethacin. The preferred non-steroidal anti-inflammatory agents include flurbiprofen, piroxicam, tolmetin sodium, ibuprofen, naproxen, indomethacin and tenidap. Tenidap (CP-66,248-2) is available from Pfizer Central Research (Groton, Conn.).

The non-steroidal anti-inflammatory agent may be selected from the various classes of such compounds. Such classes include, for example, salicylates such as acetylsalicyclic acid and diflunisal; acetic acids such as indomethacin, sulindac, tolmetin, diclofenac, and etodolac; propionic acids such as flurbiprofen, naproxen, indomethacin, tolmetin sodium and ketoprofen; fenamates such as meclofenamate; oxicams such as piroxicam; and oxindoles such as tenidap.

The amount of the non-steroidal anti-inflammatory agent is an amount which, when combined with the effectively anti-collagenase amount of tetracycline, results in a significant reduction of bone loss in mammals suffering from tissue-destructive conditions associated with excess metalloproteinase activity. The amount depends on the particular anti-inflammatory agent used, the mammal to which the composition is administered, and the amount of the tetracycline in the composition. Some typical doses for routine human use include, for example, 20 mg/day for piroxicam, 150 mg/day for indomethacin, 1600–1800 mg/day for lolmetin, 1000 mg/day for naproxen, and 3200 mg/day for ibuprofen.

For example, a suitable amount of a CMT such as 4-dedimethylamino tetracycline is 15 mg/kg. A suitable mount of anti-inflammatory agent in combination with 30 mg/kg of a CMT such as 4-dedimethylamino tetracycline would be, for example, 1–8 mg/kg flurbiprofen, 0.3 mg/kg piroxicam and 40 mg/kg ibuprofen. As a guideline for providing the proper amount of anti-inflammatory agents for implementing the present invention, a rule of thumb is to administer an amount which is 20% to 80% of the conventional anti-inflammatory dose for treating arthritis. Thus, the dosage could be from as small as 10 mg/person/day for piroxicam, to as great as 3200 mg/person/day for ibuprofen. In any event, the practitioner is guided by skill and knowledge in the field and the present invention includes without limitation dosages which arc effective to achieve the described phenomenon. For example, the non-steroidal anti-inflammatory agent my be administered in an amount of from about 0.3 mg/kg per day to about 3,500 mg per person per day.

Thus, without undue experimentation, one of ordinary skill in the art can readily vary the dosage, form and/or method of administration, with respect to a particularly selected CMT of the instant invention, so as to provide a product of manufacture for the effective treatment for a patient inflicted with HIV and/or AIDS.

Although the invention preferably contemplates treatment of the tissues of the body of a patient inflicted with the HIV and/or AIDS viruses, it is equally applicable to the treatment of any disease which causes the biochemical formation of metalloproteinase and any of its species, elastase, gelatinase, collagenase, and the like, within any tissue in the body of a patient.

The term "analog" and its variants as broadly used herein, is meant to include other related species such as homologs of tetracycline.

The terms "non-antimicrobial," "non-antibiotic," and "non-antibacterial," are meant to have equivalent definitions as used herein.

The term "biochemical" as used herein is intended to refer to biotechnology.

Although the invention has been described with reference to certain preferred embodiments, it will be appreciated that many variations and modifications may be made within the scope of the broad principles of the invention. Hence, it is intended that the preferred embodiments and all of such variations and modifications be included within the scope and spirit of the invention, as defined by the following claims.

I claim:

1. A method for healing HIV viral infections, or AIDS comprising administering to patients in need of such treatment an anti-retroviral amount of non-antimicrobial, non-antibiotic, non-antibacterial chemically modified tetracycline (CMT) analogs.

2. The method of claim 1, wherein the chemically modified tetracycline (CMT) is selected from the group consisting of:

4-dedimethylaliiinotetracycline,
4-dedimtntnhylamino-oxytetracycline,
4-dedimethylamino-7-chlortetracycline,
4-hydroxy-4-dedimethylaminotetracycline,
5a,6-anhydro-4-hydroxy-4-dedimethylaminotetracycline,
6-alpha-dcoxy-5-hydroxy-4-dedimethylaminotetracycline,
6-dernethyl-6-deoxy-4-dedimelhylaminotetracycline,
4-dedimethylamino-11-hydroxy-12a-deoxytetracyclins,
12a-deoxy-4-deoxy-4-dedimethylaminotetracycline,
6-alpha-deoxy-5-hydroxy-4-dedimethylaminodoxycycline,
12a,4a-anhydro-4-dedimethylaminotetracycline, minocycline-CMT,
7-dimethylamino-6-demethyl-6-deoxy-4-dedimethylaminotetracycline,
6a-benzylthiomethylenetetracycline,
the 2-nitrilo analogs of tetracycline (tetracyclinonitrile),
the mono-N-alkylated amide of tetracycline,
6-fluoro-6-demethyltetracycline,
11a-chlortetracycline,
tetracycline pyrazole,
12a-deoxytetracycline,
4-dedimethylamino-5-oxytetracycline,
5a,6-anhydro-4-hydroxy-4-dedimethylaminotetracycline,
12a,4a-anhydro-4-dedimethylaminotetracycline,
tetracyclonitrile,
7-chloro-4-dedimethylaminotetracycline,
12a-deoxy-4-deoxy-4-dedimethylaminotetracycline,
4-dedimethylamino-7-chlorotetracycline,
4-dedimethylamino-7-dedimethylaminotetracycline,
the 2-nitrilo analogs of tetracycline,
4-dedimethylamino 12a-deoyotetracycline,
tetracyclines altered at the 2-carbon position to produce a nitrile,
4-dedimethylamino-7-chlorotetracycline,
6-alpha-deoxy-5-hydroxy-4-dedimethylaminotetracycline,
tetracyclonitrile,
6-alpha-benzylthiomethyltetracycline,
the 2-nitrilo analog of tetracycline,
11-alpha-chlorotetracycline,
7-chlortetracycline,
5 hydroxytetracycline,
6-demethyl-7-chlortetracycline, 6-demethyl-6-deoxy-5-hydroxy-6-methylenetetracycline,
6-alpha-benzylthiomethylenetetracycline,
a nitrile analog of tetracycline,
a mono-N-alkylated amide of tetracycline,
2-acetyl-8-hydroxy-1-tetracycline,
6-demethyl-6-deoxytetracycline,
6-demethyl-6-deoxy-5-hydroxy-6-methylenetetracycline,
2-acetyl-8-hydroxyl-1-tetracycline,
4-hydroxy-4-dedimethylaminotetracycline,
5a,6-anhydro-4-hydroxy-4-dedimethylaminotetracycline,
6-demethyl-6-deoxy-4-dedimethylaminotetracycline,
6-deoxy-8-demethyl-4-dedimethylaminotetracycline,
6a-deoxy-5-hydroxy-4-dedimethylaminotetracycline,
tetracyclines altered at the 2-carbon position to produce a nitrile,
pyrazole derivative of tetracycline,
7-chloro-6-demethyl-4-dedimethylaminotetracycline,
11-apha-chlortetracycline,
4-dedimethylamino-7-chlortetracycline,
4-de(dimethylamino)-tetracycline,
4-de(dimethylamino)-5-oxytetracycline,
4-de(dimethylamino)-7-chlortetracycline,
7-chloro-6-demethyl-4-dedimethylaminotetracycline,
6-o-deoxy-5-hydroxy-4-dedimethylaminotetracycline,
6-alpha-obenzylthiomethylenetetracycline,
4-de(dimethylamino)-5-oxytetracycline,
4-de(dimethylamino)-7-chlortetracycline,
4-hydroxy-4-dedimethylaminotetracycline,
6-alpha-deoxy-5-hydroxy-4-dedimethylaminotetracycline,
4-de(dimethylamino)-tetracycline,
4-de(dimethylamino)-7-chlortetracycline,
7-chloro-6-demethyl-4-dedimethylaminotetracycline. dedimethylaminotetracycline
6-alpha-benzyl-thiomethylenetetracycline,
11-alpha-chlortetracycline,
6-demethyl-6-deoxy-5-hydroxy-6-methylenetetracycline,
6-fluoro-demethyltetracycline,
and the salts, conjugates, derivatives and combinations thereof.

3. The method of claim 1, wherein said analog comprises a form suitable for oral administion.

4. The method of claim 2, wherein said analog comprises a form suitable for topical application.

5. The method of claim 1, wherein said analog comprises a form suitable for administion by way of an injection or intravenous perfusion.

6. The method of claim 1, wherein said analog comprises an amount suitable for providing a dosage of from about 0.1 mg/kg/day to about 100 mg/kg/day.

7. The method of claim 6, wherein said analog comprises an amount suitable for providing a dosage of from about 10 mg per kg per day to about 50 mg per kg per day.

8. The method of claim 7, wherein said analog comprises an amount suitable for providing a dosage of from about 20 mg per kg per day to about 25 mg per kg per day.

*9. A method for treating the biochemical formation of materials incidental to HIV or AIDS or which promote the advancement of HIV or AIDS or which promote the advancement of AIDS and other opportunistic diseases to which a patient might become ill comprising administering to patients in need of such treatment an anti-retroviral amount of non-antimicrobial, non-antibiotic, non-antibacterial chemically modified tetracycline (CMT) analogs.*

*10. The method of claim 9 wherein the chemically modified tetracycline (CMT) is selected from the group consisting of:*

*4-dedimethylaliinotetracycline,*
*4-dedimethylamino-oxytetracycline,*
*4-dedimethylamino-7-chlorotetracycline,*
*4-hydroxy-4-dedimethylaminotetracycline,*
*5-alpha-6-anhydro-4-hydroxy-4-dedimethylaminotetracycline,*
*6-alpha-deoxy-5-hydroxy-4-dedimethylaminotetracycline,*
*6-dimethyl-6-deoxy-4-dedimethylaminotetracycline,*
*4-dedimethylamino-11-hydroxy-12-alpha-deoxytetracycline,*
*12-alpha-deoxy-4deoxy-4-dedimethylaminotetracycline,*
*6-alpha-deoxy-5-hydroxy-4-dedimethylaminotetracycline,*
*12-alpha,4alpha-anhydro-4-dedimethylaminotetracycline,*
*minocycline-CMT,*
*7-dimethylamino-6-dimethyl-6-deoxy-4-dedimethylaminotetracycline,*
*6-alpha-benzylthiomethylenetetracycline,*
*the 2-nitrilo analogs of tetracycline (tetracyclinonitrile),*
*the mono-N-alkylated wide of tetracycline,*
*6-fluoro-6-demethyltetracycline,*
*11alpha-chlorotetracycline,*
*tetracycline pyrazole,*
*12-alpha-deoxytetracycline,*
*4-dedimethylamino-5-oxytetracycline,*
*5-alpha, 6-anhydro-4-hydroxy-4-dedimethylaminotetracycline,*
*12-alpha, 4alpha-anhydro-4-dedimethylaminotetracycline,*
*tetracyclonitrile,*
*7-chloro-4-dedimethylaminotetracycline,*
*12-alpha-4-deoxy-4-dedimethylaminotetracycline,*
*4-dedimethylamino-7-chlorotetracycline,*
*4-dedimethylamino-7-dedimethylaminotetracycline,*
*the 2-nitrilo analogs of tetracycline,*
*4-dedimethylamino-12alpha-deoxyotetracycline,*
*tetracyclines altered at the 2-carbon position to produce a nitrile,*
*4-dedimethylamino-7-chlorotetracycline,*
*6-alpha-deoxy-5-hydroxy-4-dedimethylaminotetracycline,*
*tetracyclonitrile,*
*6-alpha-benzylthiomethyltetracycline,*
*the 2-nitrilo analog of tetracycline,*
*11-alpha-chlorotetracycline,*
*7-chlortetracycline,*
*5-hydroxytetracycline,*
*6-demethyl-7-chlorotetracycline,*
*6-demethyl-6-deoxy-5-hydroxy-6-methylenetetracycline,*
*6-alpha-benzylthiomethylenetetracycline,*

*a nitrile analog of tetracycline,*

*a mono-N-alkylated amide of tetracycline,*

*2-acetyl-8-hydroxy-1-tetracycline,*

*6-demethyl-6-deoxytetracycline,*

*6-demethyl-6-deoxy-5-hydroxy-6-methylenetetracycline,*

*2-acetyl-8-hydroxyl-1-tetracycline,*

*4-hydroxy-4-dedimethylaminotetracycline,*

*5-alpha, 6-anhydro-4-hydroxy-4-dedimethylaminotetracycline,*

*6-demethyl-6-deoxy-4-dedimethylaminotetracycline,*

*6-deoxy-8-demethyl-4-dedimethylaminotetracycline,*

*6-alpha-deoxy-5-hydroxy-4-dedimethylaminotetracycline,*

*tetracyclines altered at the 2-carbon position to produce a nitrile,*

*pyrazole derivative of tetracycline,*

*7-chloro-6-demethyl-4-dedimethylaminotetracycline,*

*11-alpha-chlorotetracycline,*

*4-dedimethylamino-7-chlorotetracycline,*

*4-de(dimethylamino)-tetracycline,*

*4-de(dimethyl)-5-oxytetracycline,*

*4-de(dimethylamino)-7-chlorotetracycline,*

*7-chloro-6-demethyl-4-dedimethylaminotetracycline,*

*6-alpha-deoxy-5-hydroxy-4-dedimethylaminotetracycline,*

*6-alpha-obenzylthiomethylenetetracycline,*

*4-de(dimethylamino)-5-oxytetracycline,*

*4-de(dimethylamino)-7-chlorotetracycline,*

*4-hydroxy-4-dedimethylaminotetracycline,*

*6-alpha-deoxy-5-hydroxy-4-dedimethylaminotetracycline,*

*4-de(dimethylamino)-tetracycline,*

*4-de(dimethylamino)-7-cholorotetracycline,*

*7-chloro-6-demethyl-4-dedimethylaminotetracycline,*

*dedimethylaminotetracycline,*

*6-alpha-benzyl-thiomethylenetetracycline, 11-alpha-chlorotetracycline,*

*6-demethyl-6-deoxy-5-hydroxy-6-methylenetetracycline,*

*6-fluoro-demethyltetracycline,*

*and the salts, conjugates, derivatives and combinations thereof.*

*11. The method of claim 9 wherein said analog comprises a form suitable for oral administration.*

*12. The method of claim 10 wherein said analog comprises a form suitable for topical application.*

*13. The method of claim 9 wherein said analog comprises a form suitable for administration by way of an injection or intravenous perfusion.*

*14. The method of claim 9 wherein said analog comprises an amount suitable for providing a dosage of from about 0.1 mg/kg/day to about 100 mg/kg/day.*

*15. The method of claim 14 wherein said analog comprises an amount suitable for providing a dosage of from about 10 mg per kg per day to about 50 mg per kg per day.*

*16. The method of claim 15 wherein said analog comprises an amount suitable for providing a dosage of from about 20 mg per kg per day to about 25 mg per kg per day.*

* * * * *